United States Patent [19]

Chikama

[11] Patent Number: 4,986,257
[45] Date of Patent: Jan. 22, 1991

[54] BENDING DEVICE

[75] Inventor: Toshio Chikama, Tokyo, Japan

[73] Assignee: Kabushiki Kaisha Machida Seisakusho, Tokyo, Japan

[21] Appl. No.: 558,491

[22] Filed: Jul. 27, 1990

[30] Foreign Application Priority Data

| Jul. 31, 1989 | [JP] | Japan | 1-196706 |
| Jul. 31, 1989 | [JP] | Japan | 1-196707 |
| Jul. 31, 1989 | [JP] | Japan | 1-196708 |

[51] Int. Cl.$^5$ .............................................. A61B 1/00
[52] U.S. Cl. ........................................................ 128/4
[58] Field of Search ...................................... 128/4, 6

[56] References Cited

U.S. PATENT DOCUMENTS

| 4,483,326 | 11/1984 | Yamaka et al. | 128/4 |
| 4,718,407 | 1/1988 | Chikama | 128/4 |
| 4,721,099 | 1/1988 | Chikawa | 128/4 |
| 4,834,069 | 5/1989 | Umeda | 128/4 |
| 4,905,666 | 3/1990 | Fukuda | 128/4 |
| 4,941,455 | 7/1990 | Watanabe et al. | 128/4 |

FOREIGN PATENT DOCUMENTS 53-52306 12/1978 Japan .
56-121532 9/1981 Japan .
56-163403 12/1981 Japan .

Primary Examiner—William H. Grieb
Attorney, Agent, or Firm—Fish & Richardson

[57] ABSTRACT

A bending device has a simplified construction for bending a bending portion. A wire is disposed in opposed relation to a manipulation hole formed in a body. When the finger is inserted into the manipulation hole to press the wire in a direction perpendicular to the longitudinal direction of the wire, the wire is pulled to bend the bending portion. Instead of the wire, an operating member can be disposed in opposed relation to the manipulating hole, in which case a manipulating force of the finger is converted through the operating member into a force to pull the wire. The operating member operatively connected to the wire may be of the type slidably supported on the body, and may be of the type integrally connected to the body through a neck portion.

19 Claims, 10 Drawing Sheets 4,986,257

BENDING DEVICE

BACKGROUND OF THE INVENTION

This invention relates to a bending device such as an endoscope and a catheter.

Generally, an endoscope comprises a body, an insertion portion extending from the body, a bending portion extending from a distal end of the insertion portion, and a rigid portion provided at a distal end of the bending portion. The rigid portion has an inspection window and an illumination light window. The operator bends the bending portion to direct the rigid portion in a desired direction so as to observe a cavity in the body of the patient.

Bending mechanisms for bending a bending portion of such an endoscope are disclosed in U.S. Pat. No. 4,834,069 and Japanese Laid-Open (Kokai) patent application No. 121532/81. More specifically, a manipulation knob is mounted on the outside of a body, and the manipulation knob is connected to a pulley, mounted within the body, via a shaft extending through the body. Wires are fixedly connected at their proximal ends to the pulley. The wires extend through the bending portion and an insertion portion, and are fixedly connected at their distal ends to the distal end of the bending portion. When the pulley is angularly moved, one of the wires corresponding to this angular movement is pulled to bend the bending portion.

Japanese Utility Model Publication No. 52306/78 discloses a bending mechanism with a pulley and also a bending mechanism using a pinion and racks in mesh therewith, instead of a pulley. In the latter mechanism, the pinion is connected to a manipulation knob via a shaft, and wires are fixedly connected at their proximal ends to the racks, respectively.

The above conventional bending mechanisms employ either the manipulation knob and the pulley or the manipulation knob and the rack-and-pinion arrangement, and because of such a construction, the weight is increased. In addition, since either the pulley or the rack-and-pinion arrangement is mounted within the body, the body has an increased size. This results in a problem that the operator becomes fatigued relatively soon. Further, for operating such a bending mechanism, the operator holds the body with one hand, and angularly moves the manipulating knob with the fingers of this hand. This requires much skill.

U.S. Pat. No. 4,721,099 shows, in FIG. 17, a bending mechanism having a joy stick as an operating (manipulating) member. This bending mechanism has a drawback that a construction for supporting the joy stick is complicated, which increases the cost and the size of the body.

Japanese Laid-Open Utility Model application No. 163403/81 discloses an endoscope in which a rubber tube is fitted on a grip portion of a body.

There are U.S. patent application Ser. No. 407,314 filed on Sept. 14, 1989 now Pat. No. 4,944,455, and its West German counterpart (patent application No. P 3931719.6) disclosing a bending mechanism in which a wire-passing portion and a retainer portion for retaining a proximal end of a wire are provided within a body, and that of the wire disposed between the wire-passing portion and the retainer portion is pulled in the longitudinal direction of the wire.

SUMMARY OF THE INVENTION

It is an object of this invention to provide a bending device which can have a lightweight body, and can be manufactured at low costs, and can effect a bending operation relatively easily.

According to a first aspect of the invention, there is provided a bending device comprising:
(a) a hollow body;
(b) an insertion portion extending from the body;
(c) a bending portion extending from a distal end of the insertion portion; and
(d) a wire fixedly connected at its distal end to a distal end of the bending portion and having a proximal end disposed in the body, the wire extending through the bending portion and the insertion portion into the body;
(e) the body having a manipulation hole into which the finger is adapted to be inserted, a guide portion through which the wire is passed and a retainer portion for retaining the proximal end of the wire being formed on an inner surface of the body, the guide portion and the retainer portion being disposed in opposed relation to each other, the manipulation hole being disposed between the guide portion and the retainer portion, part of the wire being disposed in the manipulation hole, and the wire receiving a force applied, in a direction perpendicular to a longitudinal direction of the wire, by the finger inserted in the manipulation hole, so that the wire is pulled to bend the bending portion.

According to a second aspect of the invention, there is provided a bending device comprising:
(a) a hollow body having a manipulation hole into which the finger is adapted to be inserted;
(b) an insertion portion extending from the body;
(c) a bending portion extending from a distal end of the insertion portion;
(d) a wire fixedly connected at its distal end to a distal end of the bending portion and having a proximal end disposed in the body, the wire extending through the bending portion and the insertion portion and into the body; and
(e) operating means for converting a force, applied by the finger inserted into the manipulation hole, into a force to pull the wire so as to bend the bending portion, the operating means being disposed inside of the body in opposed relation to the manipulation hole.

According to a third aspect of the invention, there is provided a bending device comprising:
(a) a hollow body;
(b) an insertion portion extending from the body;
(c) a bending portion extending from a distal end of the insertion portion;
(d) a wire fixedly connected at its distal end to a distal end of the bending portion and having a proximal end disposed in the body, the wire extending through the bending portion and the insertion portion and into the body; and
(e) an operating member slidably supported on the body. the operating member being operatively connected to the wire, and upon sliding movement of the operating member relative to the body, the wire being pulled to bend the bending portion.

According to a fourth aspect of the invention, there is provided a bending device comprising:
(a) a hollow body of a resin;

(b) an insertion portion extending from the body;

(c) a bending portion extending from a distal end of the insertion portion;

(d) a wire fixedly connected at its distal end to a distal end of the bending portion and having a proximal end disposed in the body, the wire extending through the bending portion and the insertion portion into the body; and (e) an operating member integrally formed on the body through a neck portion integral with the body, the operating member being pivotal about the neck portion, the operating member being operatively connected to the wire, and upon pivotal movement of the operating member, the wire being pulled to bend the bending portion.

DESCRIPTION OF THE PREFERRED EMBODIMENTS OF THE INVENTION

Figure 1:
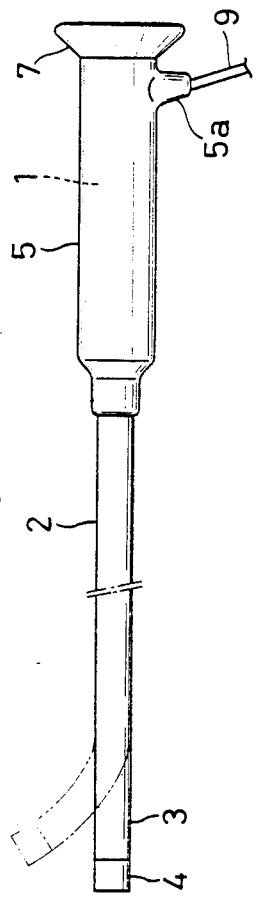
FIG. 1 is a side-elevational view of an endoscope (bending device) according to the present invention.

Preferred embodiments of the invention will now be described with reference to the drawings.

An endoscope shown in FIGS. 1 to 4 comprises an elongated, cylindrical body 1, a flexible insertion portion 2 extending from a distal end of the body 1, a flexible bending portion 3 extending from a distal end of the insertion portion 2, and a rigid portion 4 mounted on a distal end of the bending portion 3.

The body 1 is made of a material of a relatively high rigidity such as a rigid plastics material. The body 1 may be molded into a cylindrical shape from the beginning or may be formed by bonding together two semi-cylindrical molded members defining halves of a cylinder, respectively. The body 1 is reduced in diameter at its distal end portion, and the proximal end portion of the insertion portion 2 is fixedly fitted in the distal end portion of the body 1. A sheath tube 5, made of a soft and elastic material such as rubber, is tightly fitted around the body 1 and the proximal end portion of the insertion portion 1, the sheath tube 5 covering the entire length of the body 1 except for its proximal end.

The rigid portion 4 has an inspection window and an illumination window both of which are not shown. An ocular portion 7 having an ocular lens 6 is provided at the proximal end of the body 1. The ocular lens 6 is optically connected to an objective lens via an image guide 8 made of optical fibers, this objective lens being disposed in the vicinity of the inspection window of the rigid portion 4. A flexible tube (not shown) extends from the peripheral wall of the body 1 adjacent to its proximal end. A cylindrical connector is attached to a distal end of this flexible tube. A light guide 9 made of optical fibers is connected at one end to a distal end of the connector. The light guide 9 extends through the connector, the flexible tube, the body 1, the insertion portion 2 and the bending portion 3, and the other end of the light guide 9 is disposed at the illumination window of the rigid portion 4. The connector is connected to a light source (not shown), and in this condition illumination light from the light source is transmitted through the light guide 9, and is emitted from the illumination window.

The sheath tube 5 has a projection 5a having a hole therethrough, and the intermediate portion of the light guide 9 is fitted in and supported by the hole of the projection 5a, and the proximal end of the flexible tube is fitted on and supported by the projection 5a.

Figure 2:
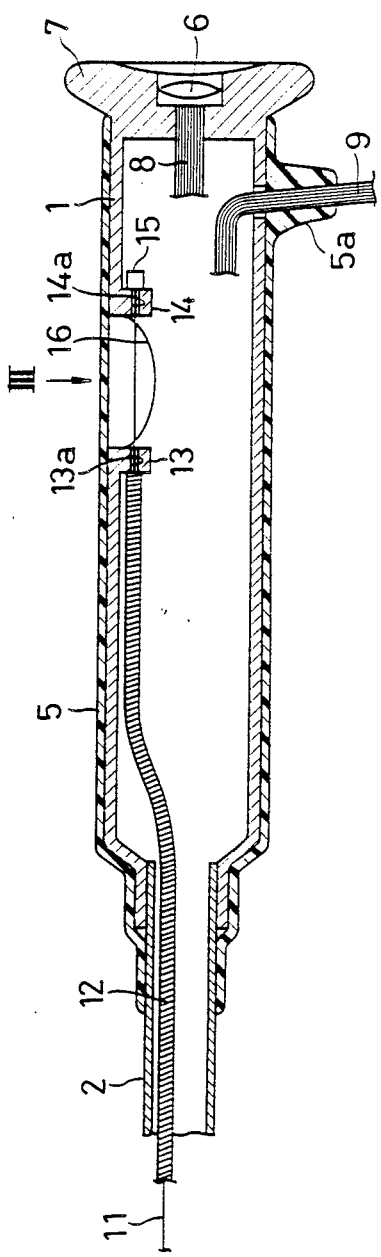
FIG. 2 is an enlarged, vertical longitudinal cross-sectional view of an important portion of the endoscope.

Next, a mechanism for bending the bending portion 3 in one direction will now be described. As shown in FIG. 2, this mechanism includes a wire 11 received in the endoscope. A distal end of the wire 11 is fixedly connected to an upper portion (FIG. 1) of the distal end of the bending portion 3. The wire 11 extends through the bending portion 3 and the insertion portion 2 into the body 1. The wire 11 is passed through a guide tube 12. The guide tube 12 is made of a wire element tightly wound into a coil-shape. A distal end of the guide tube 12 is fixedly secured to the distal end of the insertion portion and hence to the proximal end of the bending portion 3. The guide tube 12 extends through the insertion portion 2 into the body 1.

Two projections 13 and 14 are formed on the inner peripheral surface of the body 1, and are spaced from each other along the length of the body 1. More specifically, the two projections 13 and 14 are disposed on a straight line parallel to the axis of the body 1. The two projections 13 and 14 have respective insertion holes 13a and 14a formed therethrough and extending along the axis of the body 1. The wire 11 is passed through the insertion holes 13a and 14a. A stop member 15 greater in diameter than the insertion holes 13a and 14a is fixedly secured to the proximal end of the wire 11. When the bending portion 3 is in a straight condition, the stop member 15 is held against the projection 14 disposed close to the proximal end (the right end in the drawings) of the body 1. The projection 13 remote from the proximal end of the body 1 serves as a guide portion which supports the wire 11 in such a manner as to allow the movement of the wire 11 in its longitudinal direction and to limit the movement of the wire 11 in a direction perpendicular to the longitudinal direction of the wire 11. The projection 14 close to the proximal end of the body 11 serves as a retainer portion which retains the wire 11 against movement in its longitudinal direction and also against movement in a direction perpendicular to this longitudinal direction. The proximal end of the guide tube 12 is retained by or fixed to the projection 13.

Figure 3:
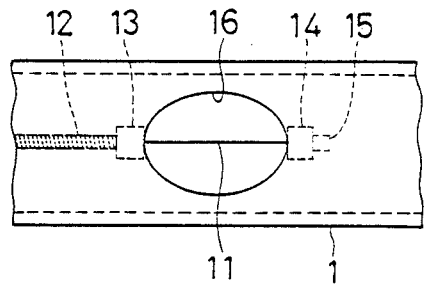
FIG. 3 is a fragmentary view of a body of the endoscope as seen in a direction indicated by arrow III of FIG. 2, with a sheath member omitted.
Figure 4:
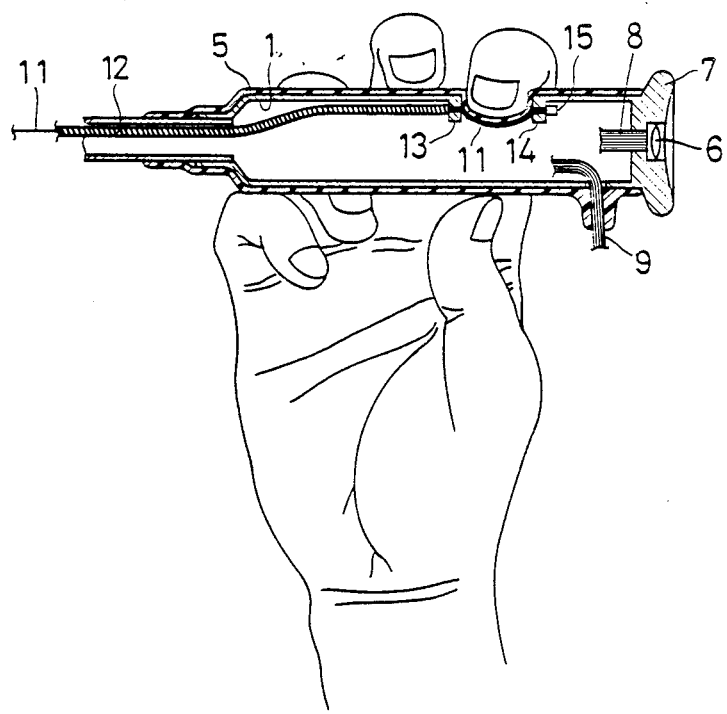
FIG. 4 is a cross-sectional view of the endoscope held by the hand, showing a bending operation.

As shown in FIGS. 2 and 3, a manipulation hole 16 is formed through the peripheral wall of the body 1 intermediate the opposite ends of the body 1. The manipulation hole 16 is disposed between the two projections 13 and 14. Therefore, that portion of the wire 11 lying between the two projections 13 and 14 is substantially disposed in the manipulation hole 16. The wire 11 is disposed between lower portions of the peripheral edges of the manipulation hole 16 and an imaginary arcuate surface covering the manipulation hole 16 and disposed in the outer peripheral surface of the body 1. The manipulation hole 16 is covered by the sheath tube 5, so that the internal space of the body 10 is interrupted from the exterior.

In the endoscope of the above construction, when the bending portion 3 is to be bent upwardly, the thumb, the ring finger and the little finger are put on the lower side of the body 1 while the middle finger is put on the upper side of the body 1, thus supporting the body 1 with these four fingers. In this case, the thumb is disposed just below the manipulation hole 16. Then, that portion of the sheath tube 5 covering the manipulation hole 16 is pressed by the index finger, so that the distal end portion of the index finger is inserted into the body 1 through the manipulation hole 16, together with the sheath tube 5. As a result, the distal end portion of the index finger presses the wire 11 through the sheath tube 5 in a direction perpendicular to the longitudinal direction of the wire 11. At this time, since the proximal end of the wire 11 is retained by the projection 14 through the stop member 15, the wire 11 is pulled, so that the bending portion 3 is bent.

The endoscope of this embodiment does not need a manipulation knob and either of a pulley and a rack-and-pinion arrangement which are required for a conventional endoscope. Therefore, the weight and size of the body 1 can be reduced.

In the endoscope of this embodiment, the bending portion 3 can be easily bent by a pressure (manipulating force) of the finger. Further, the lower portions of the peripheral edge of the manipulation hole 16 is disposed below the wire 11, and therefore for operating the wire 11, the distal end portion of the index finger need only be inserted into the manipulation hole 16 in a generally extended condition, without directing the distal end portion of the index finger downward. Thus, the operability is enhanced.

In the endoscope of this embodiment, the elastic sheath tube 5 is intimately fitted on the outer periphery of the body 1, and therefore when sterilizing the endoscope, sterilizing liquid or gas is prevented from intruding into the body 1.

Next, other embodiments of the invention will now be described. Those portions of these other embodiments corresponding respectively to those of the preceding embodiment are designated respectively by identical reference numerals, and detailed explanation of such corresponding portions will be omitted.

Figure 5:
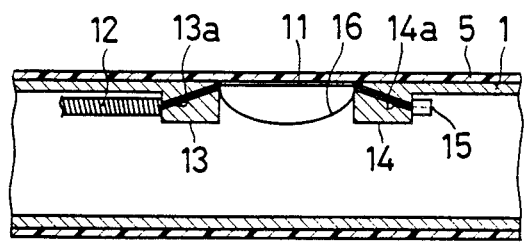
FIGS. 5 to 8 are cross-sectional views of important portions of modified bending devices, respectively.

In an embodiment shown in FIG. 5, insertion holes 13a and 14a are inclined relative to the axis of the body 1, and one end of each of the insertion holes 13a and 14a close to the manipulation hole 16 is disposed near the sheath tube 5. With this arrangement, that portion of the wire 11 disposed in the manipulation hole 16 is disposed immediately adjacent to the sheath tube 5. In this embodiment, since the wire 11 is thus disposed very close to the sheath tube 5, the degree of insertion of the finger into the body 1 to operate the wire 11 can be smaller than that in the embodiment of FIGS. 1 to 4. Therefore, the bending operation can be effected more easily.

Figure 6:
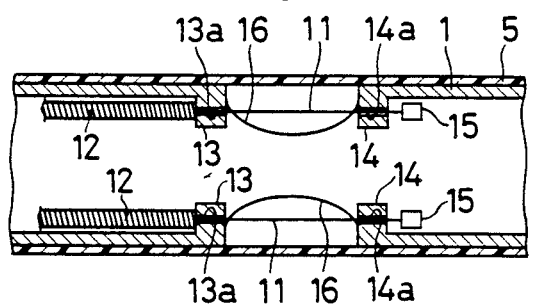

In an embodiment shown in FIG. 6, two wires 11 are used. Distal ends of the two wires 11 are fixedly connected respectively to diametrically-opposite upper and lower portions of the distal end of a bending portion 3 (FIG. 1) which are circumferentially spaced 180° from each other. A pair of manipulation holes 16 are formed through the upper and lower portions of the body, and are disposed in opposed relation to each other. Two projections 13 and 14 are formed on each of upper and lower portions of the inner peripheral surface of the body 1, and the manipulation hole 16 is disposed between the two projections 13 and 14. The upper wire 11 is passed through insertion holes 13a and 14a formed respectively through the upper projections 13 and 14, and similarly the lower wire 11 is passed through insertion holes 13a and 14a formed respectively through the lower projections 13 and 14, and that portion of each wire 11 disposed between the two projections 13 and 14 is substantially disposed in the mating manipulation hole 16.

In the embodiment of FIG. 6, by inserting the finger (for example, the index finger) into the upper manipulation hole 16, the upper wire 11 is pulled to bend the bending portion 3 upwardly. Also, by inserting the thumb into the lower manipulation hole 16, the lower wire 11 is pulled to bend the bending portion 3 downwardly.

In the embodiment of FIG. 6, when the bending portion 3 is in a straight condition, stop members 15 secured respectively to the proximal ends of the upper and lower wires 11 are spaced apart from the upper and lower projections 14, respectively. The reason for this will now be described. When one of the wires 11 is pulled to bend the bending portion 3, the other wire 11 disposed at the outward side of the bending portion 3 need to be longer than when the bending portion 3 is in its straight condition. Therefore, the other wire 11 is moved toward the bending portion 3 within the body. This movement is possible since the stop member 15 is spaced apart from the projection 14. Let's assume that the two stop members 15 are abutted respectively against the upper and lower projections 14 when the bending portion 3 is in its straight condition. In this case, when one of the two wires 11 is pulled so as to bend the bending portion 3, the other wire 11 offers a resistance to such pulling to thereby prevent the bending of the bending portion 3.

In the embodiment of FIG. 6, when the wire 11 is pressed by the finger, a pulling force is not applied to the wire 11 until the stop member 15 is brought into contact with the projection 14. Therefore, the amount of operation (insertion) of the finger is relatively large.

Figure 7:
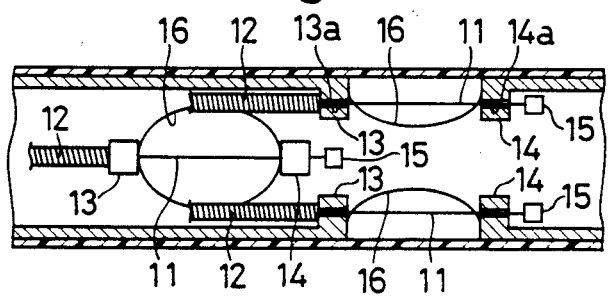

In an embodiment of FIG. 7, four wires 11 (only three of which are shown) are used so as to bend a bending portion 3 in four directions, that is, upper, lower, right and left directions. Distal ends of the four wires 11 are fixedly connected to the distal end of the bending portion 3 (FIG. 1), and are circumferentially spaced 90° from each other. Four manipulation holes 16 (only three of which are shown) are formed through the peripheral wall of the body 1, and are circumferentially spaced from one another at equal intervals. Four pairs of projections 13 and 14 (only three pairs shown) are formed on the inner peripheral surface of the body 1. The two manipulation holes 16 for bending the bending portion 3 in the upper and lower directions are spaced along the axis of the body 1 from the other two manipulation holes 16 for bending the bending portion 3 in the right and left directions. If the four manipulation holes 16 are provided at the same circumferential area of the body 1, the strength of the body 1 is much lowered.

Figure 8:
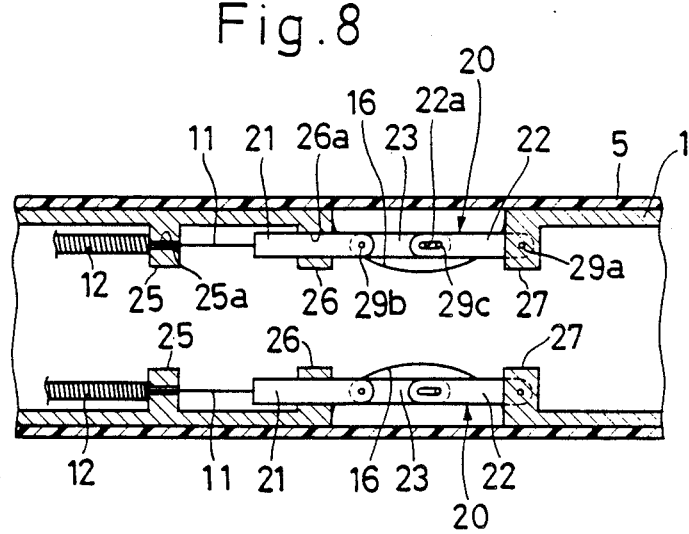

In an embodiment of FIG. 8, a bending portion can be bent in two directions. Proximal ends of two wires 11 are connected to two link mechanisms (operating means) 20, respectively. Each of the link mechanism 20 comprises three links 21, 22 and 23. Two manipulation holes 16 are formed through a peripheral wall of a body 1 as described above for the embodiment of FIG. 6, and two groups of projections 25, 26 and 27 are formed on the inner peripheral surface of the body 1. The projections 25, 26 and 27 of each group are disposed on a straight line parallel to the axis of the body 1, and are spaced from one another along the axis of the body 1. The intermediate projection 26 and the projection 27 close to the proximal end (the right end in the drawings) of the body 1 are disposed in opposed relation to each other, with the manipulation hole 16 disposed therebetween. The projection 25 remote from the proximal end of the body 1 and the intermediate projection 26 have respective insertion holes 25a and 26a formed therethrough and extending along the axis of the body 1. A proximal end of a guide tube 12 for guiding the wire 11 is retained by or fixed to the projection 25, and the wire 11 is passed through the insertion hole 25a of the projection 25. The insertion hole 26a of the intermediate projection 26 is greater in diameter than the insertion hole 25a of the projection 25, and the first link 21 extends through the insertion hole 26a for sliding movement along the axis of the body 1. The proximal end of the wire 11 is connected to the distal end of the first link 21. The second link 22 is pivotally connected at its proximal end to the projection 27 by a pin 29a. The opposite ends of the third link 23 are pivotally connected to the proximal end of the first link 21 and the distal end of the second link 22 by pins 29b and 29c.

The projection 26 serves as a support member slidably supporting the first link 21. The projection 27 serves as a support member pivotally supporting the second link 22.

The axis of pivotal movement of the proximal end of the second link 22 relative to the projection 27, the axis of pivotal movement of the distal end of the third link 23 relative to the first link 21, and the axis of pivotal movement of the proximal end of the third link 23 relative to the second link 22 are disposed perpendicular to the axis of the body 1, and also are disposed perpendicular to the direction of operation (insertion) of the fingers as later described.

The portion of connection between the second and third links 22 and 23 will now be described in detail. A slot 22a is formed through the distal end portion of the second link 22, and extends along the length thereof. The pin 29c extending from one side of the proximal end portion of the third link 23 is received in the slot 22a. The link mechanism 20 including this connection portion is mostly disposed in the manipulating hole 16.

In the embodiment of FIG. 8, when the bending portion is in its straight condition, the pin 29c on the third link 23 is disposed at the right end of the slot 22a in the second link 22, and the three links 21, 22 and 23 are disposed on a common straight line in the longitudinal direction of the body 1. Actually, the links 22 and 23 slightly sway, and their connected ends are slightly displaced downwardly by gravity. However, for better understanding, the operation of the link mechanism 20 will now be described, assuming that there is no influence of the gravity, so that the links 22 and 23 extend along the common straight line along which the link 21 extends. For bending the bending portion upwardly, the index finger is inserted in the upper manipulation hole 16 to press the connecting portion between the second and third links 22 and 23 of the link mechanism 20 through the sheath tube 5. As a result, the two links 22 and 23 are brought into a folded condition, so that the pin 29c moves along the slot 22a and reaches the left end of the slot 22a. When the above connecting portion is further pressed, the manipulating (operating) force applied by the finger is transmitted to the upper wire 11 via the link mechanism 20, so that the upper wire 11 is pulled to bend the bending portion upwardly. At this time, the lower wire 11 is disposed at the outward side of the bending portion, and the lower wire 11 is moved toward the bending portion, that is, to the left (FIG. 8) as the bending operation proceeds. In the link mechanism 20 connected to the lower wire 11, the pin 29c on the third link 23 moves along the slot 22a in the second link 22 in the left direction, thereby allowing the movement of the wire 11.

When the link mechanism 20 of FIG. 8 is applied to an endoscope adapted to be bent in only one direction, instead of the slot 22a, a circular hole for passing the pin 29b of the third link 23 therethrough is merely formed through the second link 22.

Figure 9:
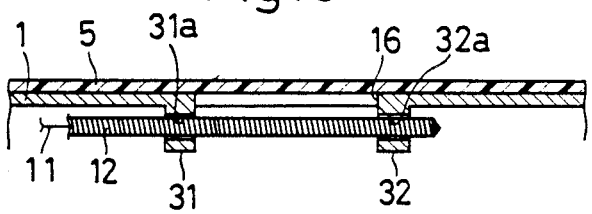
FIG. 9 is a fragmentary cross-sectional view of a further modified bending device in its inoperative condition.
Figure 10:
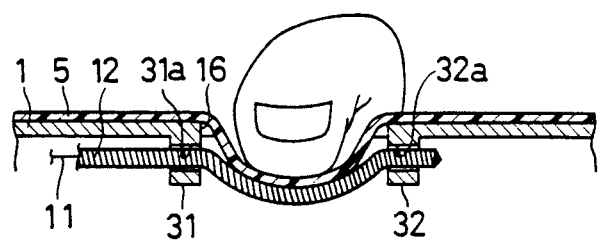
FIG. 10 is a view similar to FIG. 9, but showing an operative condition of the bending device of FIG. 9.
Figure 11:
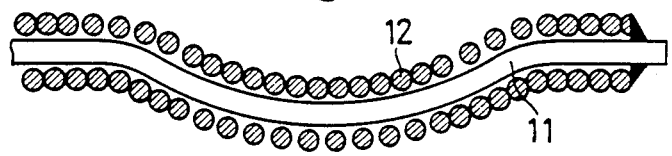
FIG. 11 is an enlarged cross-sectional view, showing a guide tube and a wire in the bending device of FIG. 9.

In an embodiment shown in FIGS. 9 to 11, a pair of projections 31 and 32 are formed on an inner peripheral surface of a body 1, and are spaced from each other along the length of the body 1. The two projections 31 and 32 are disposed in opposed relation to each other, with a manipulation hole 16 interposed therebetween. Insertion holes 31a and 32a, which are greater in diameter than the insertion holes 13a and 14a of the projections 13 and 14 of the embodiment of FIGS. 1 to 4, are formed through the projections 31 and 32, respectively, the insertion holes 31a and 32a extending in the longitudinal direction of the body 1. A proximal end portion of a guide tube 12 is slidably passed through the insertion holes 31a and 32a. Thus, the projections 31 and 32 serve as support portions supporting the guide tube 12. A proximal end of a wire 11 is fixedly connected to the proximal end of the guide tube 12 by fastening means such as welding and brazing.

When a manipulating force is not applied by the finger, the proximal end portion of the guide tube 12 is kept straight due to its own resiliency, as shown in FIG. 9. For bending a bending portion, the finger is inserted in the manipulation hole 16 to press the proximal end portion of the guide tube 12, extending between the two projections 31 and 32, through a sheath tube 5 to bend this proximal end portion, as shown in FIGS. 10 and 11, so that the length of the guide tube 12 between the projections 31 and 32 becomes longer than when it is kept straight. As a result, a pulling force is applied to the wire 11, so that the bending portion is bent. Thus, the proximal end portion of the guide tube 12 serves as operating or manipulating means for transmitting the manipulating force of the finger to the wire 11.

Figure 14:
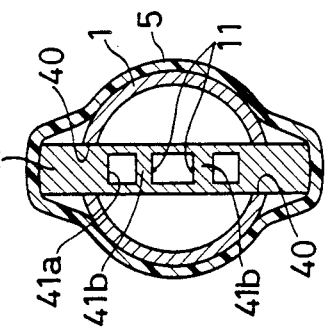
FIG. 14 is a cross-sectional view taken along the line XIV—XIV of FIG. 13.
Figure 12:
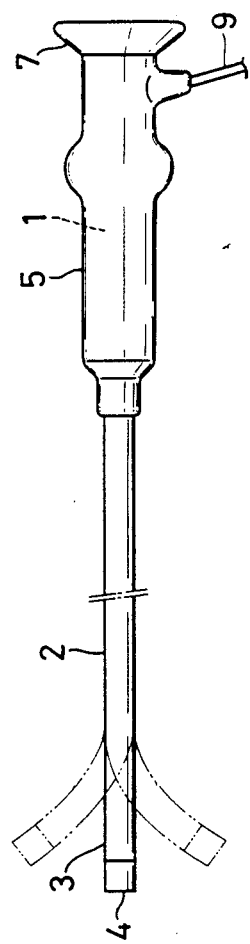
FIG. 12 is a view similar to FIG. 1, but showing a further modified endoscope (bending device)
Figure 13:
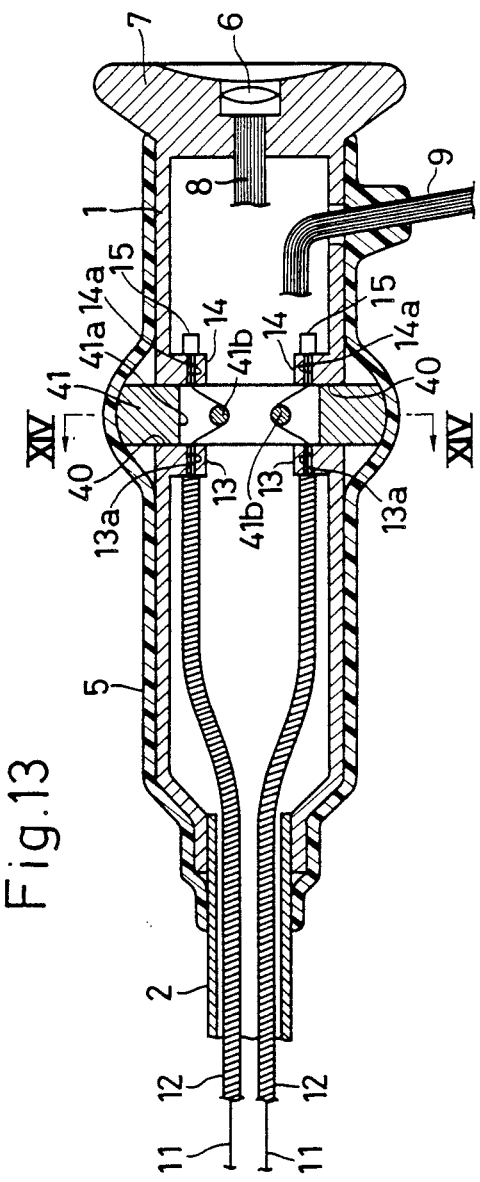
FIG. 13 is a view similar to FIG. 2, but showing the endoscope of FIG. 12.

In an embodiment shown in FIGS. 12 to 14, a bending portion 3 is bendable in two directions. A pair of guide holes 40 are formed through a peripheral wall of a body 1, and are disposed in diametrically opposite relation to each other (that is, circumferentially spaced 180° from each other). An elongated operating member 41 of a rectangular cross-section is slidably fitted in the guide holes 40. The length of the operating member 41 is sufficiently greater than the outer diameter of the body 1. Two pairs of projections 13 and 14 are formed on the inner peripheral surface of the body 1, and each pair of projections 13 and 14 are spaced from each other along the length of the body 1, and disposed in opposed relation to each other, with the guide hole 40 disposed therebetween. The functions of the projections 13 and 14 are the same as those of the projections 13 and 14 of the embodiment shown in FIGS. 1 to 4. The operating member 41 has a through hole 41a formed through its central portion in the longitudinal direction of the body 1. Two engaging portions 41b are provided at the through hole 41a. The engaging portions 41b extend perpendicularly to the axis of the body 1 and also to the longitudinal direction of the operating member 41, and are spaced from each other along the length of the operating member 41. Each of the two engaging portions 41b is displaced from insertion holes 13a and 14a of the corresponding pair of projections 13 and 14 toward the centerline or axis of the body 1. That portion of each wire 11 disposed between the insertion holes 13a and 14a is engaged with the inner side of the corresponding engaging portion 41b.

When the bending portion 3 is in its straight condition as shown in FIG. 12, the opposite end portions of the operating member 41 are projected an equal amount outwardly from the outer peripheral surface of the body 1, as shown in FIGS. 13 and 14, and each stop member 15 is abutted against the corresponding projection 14. For example, when the bending portion 3 is to be bent upwardly, the upper end of the operating member 41 is pressed through a sheath tube 5 to move the operating member 41 downward, so that the upper engaging portion 41b pulls the upper wire 11. As a result, the bending portion 3 is bent upwardly. As the operating member 41 moves downward, the lower engaging portion 41b moves toward the lower insertion holes 13a and 14a, so that the lower wire 11 is loosened. Therefore, the lower wire 11 will not prevent an upward bending of the bending portion 3. In contrast with the above, when the lower end of the operating member 41 is pressed to move the operating member 41 upward, the lower wire 11 is pulled, so that the bending portion 3 is bent downwardly.

In this embodiment, also, the whole of the body 1 including the operating member 41 is covered by the sheath tube 5, and therefore at the time of sterilization, sterilizing liquid or gas is prevented from intruding into the body 1 through a gap between the peripheral edge of each guide hole 40 and the operating member 41.

Figure 15:
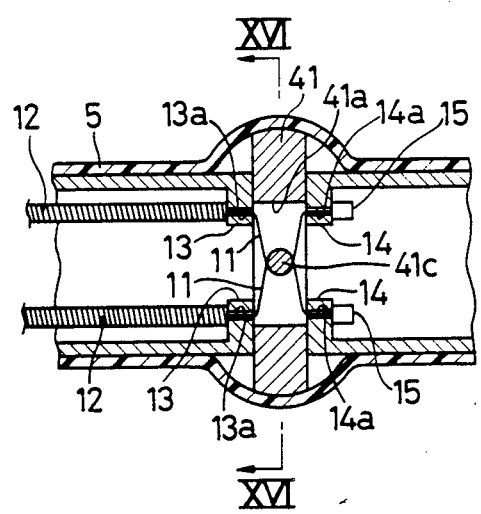
FIG. 15 is a vertical longitudinal cross-sectional view of an important portion of a further modified bending device.
Figure 16:
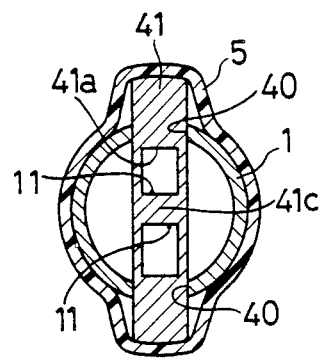
FIG. 16 is a cross-sectional view taken along the line XVI—XVI of FIG. 15.

In an embodiment shown in FIGS. 15 and 16, one engaging portion 41c is provided at a through hole 41a formed through a central portion of an operating member 41. Two wires 11 are engaged with the engaging portion 41c.

Figure 17:
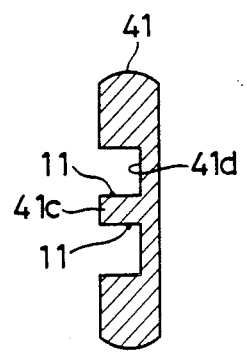
FIG. 17 is a cross-sectional view of a modified form of an operating member usable in the bending device of FIG. 15.

FIG. 17 shows a modified operating member 41. In this example, instead of the through hole 41a shown in FIGS. 15 and 16, a recess 41d is formed in the central portion of the operating member 41, and an engaging portion 41c with which the wires 11 are engaged is provided at a central portion of the recess 41d.

Figure 18:
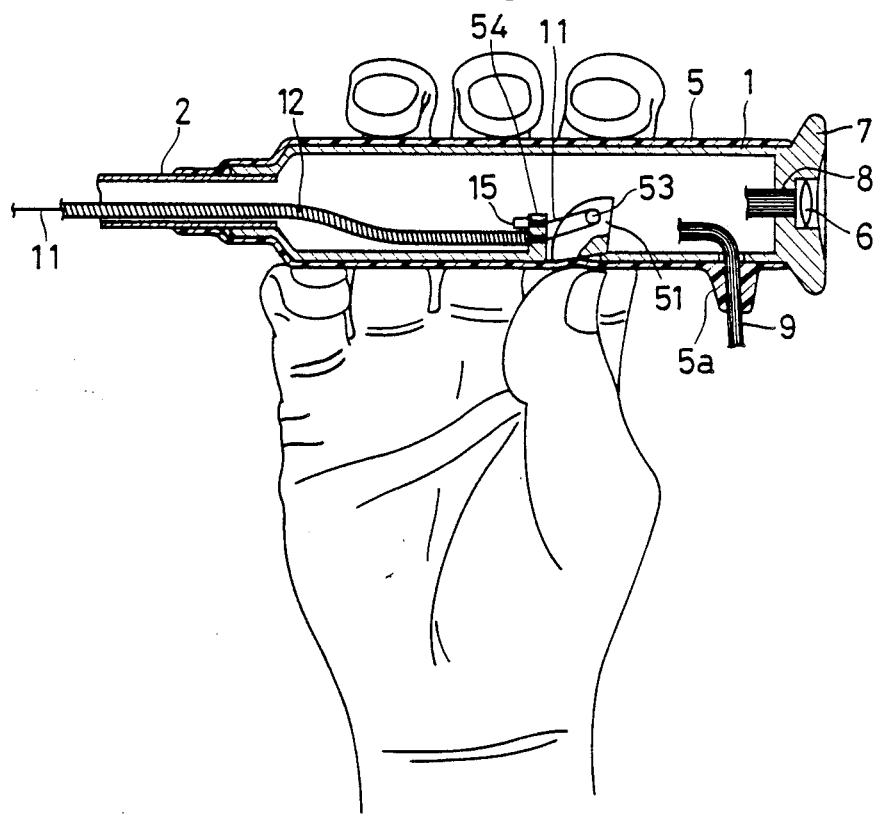
FIG. 18 is a view similar to FIG. 4, but showing a further modified endoscope (bending device)
Figure 19:
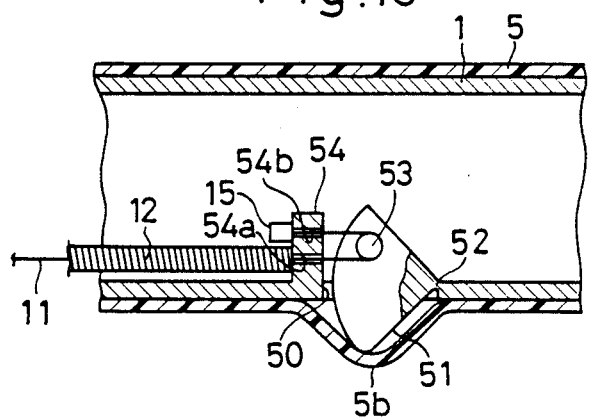
FIG. 19 is a fragmentary cross-sectional view of the bending device of FIG. 18 in its inoperative condition.

In an embodiment shown in FIGS. 18 and 19, an operating member 51 of a fan-shape is formed integrally with a lower portion of a peripheral wall of a body 1. More specifically, a hole 50 is formed through the lower portion of the peripheral wall of the body 1. The operating member 51 has a triangular or narrow end facing away from its arcuate or wide end. At the rear edge of the hole 50 close to the proximal end of the body 1, the operating member 51 is connected at its triangular end to the body 1 via a neck portion 52 of a reduced thickness. Therefore, the operating member 51 is pivotal about the neck portion 52. The axis of pivotal movement of the operating member 51 about the neck portion 52 is perpendicular to the axis of the body 1. Part of the operating member 51 is projected outwardly from the outer peripheral surface of the body 1, and the remainder of the operating member 51 is disposed in the body 1. An engaging portion 53 extending parallel to the above axis of pivotal movement is formed on the above remainder of the body 1.

A projection 54 is formed on the inner peripheral surface of the body 1 adjacent to the front edge of the hole 50 remote from the neck portion 52, the projection 54 being disposed in opposed relation to the operating member 51. Two insertion holes 54a and 54b are formed through the projection 54, and extend in the longitudinal direction of the body 1, the two insertion holes 54a and 54b being spaced from each other radially of the body 1, that is, in a upward-downward direction in the drawings. A wire 11 is passed through the lower insertion hole 54a, and is then extended or turned around the engaging portion 53 over a half of the circumference thereof, and is passed through the upper insertion hole 54b. A stop member 15 fixedly connected to the proximal end of the wire is abutted against the projection 54.

A sheath tube 5 is intimately fitted on the body 1 and a proximal end portion of an insertion portion 2. However, the sheath tube 5 has a projected portion 5b in which the outer portion of the operating member 51 projecting outwardly from the body 1 is received, so that the operating member 51 is normally not urged by the resiliency of the sheath tube 5, thus preventing the operating member 51 for being angularly movement by the resilient force of the sheath tube 5.

In the embodiment of FIGS. 18 and 19, for bending a bending portion 3, the operating member 51 is pressed through the sheath tube 5 to be pivotally moved in a clockwise direction (FIGS. 18 and 19), so that the engaging portion 53 is moved in a direction away from the projection 54. As a result, the wire 11 is pulled to bend the bending portion 3. At this time, for example, the thumb is put on the outer surface of the projected portion 5b of the sheath tube 5, and the little finger is put on the lower side of the distal end portion of the body 1, and index finger, the middle finger and the ring finger are put on the upper side of the body 1, thereby supporting the body 1, as shown in FIG. 18, and the operating member 51 is pivotally moved by the thumb. Thus, the bending operation can be effected with one hand while holding the body 1 with this hand.

Since the body 1 is covered with the sheath tube 5, sterilization liquid or the like is prevented from intruding into the body 1 through the hole 50.

Figure 20:
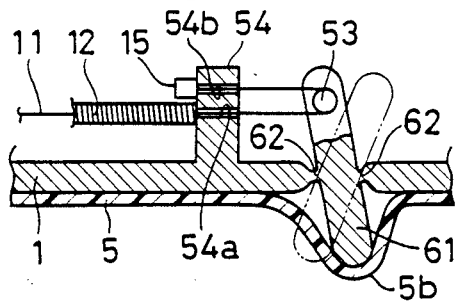
FIGS. 20 to 23 are cross-sectional views of important portions of further modified bending devices, respectively.

In an embodiment shown in FIG. 20, a bar-like operating member 61 is used. The operating member 61 is pivotally supported at its front and rear sides of its central portion to a body 1 through a pair of neck portions 62. Part of the operating member 61 is projected outwardly from the body 1, and the remainder of the operating member 61 is disposed in the body 1 and is connected to a wire 11 through an engaging portion 53. Although not shown in the drawings, in order to allow the pivotal movement of the operating member 61, one or more slits or slots are formed in that portion of the body 1 disposed immediately adjacent to each of the opposite sides of the operating member 61 spaced away from each other in a direction perpendicular to the sheet of FIG. 20. When a bending portion is in a straight condition, the operating member 61 is inclined, with the engaging portion 53 disposed close to the projection 54. For bending the bending portion, the outer end of the operating member 61 is pressed by the finger in a forward direction, so that the operating member 61 is pivotally moved in a clockwise direction. As a result, the engaging portion 53 is moved in a direction away from the projection 54 to pull the wire 11 to bend the bending portion.

Figure 21:
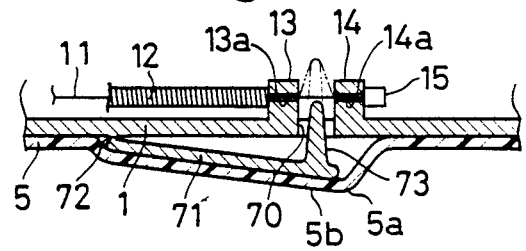

In an embodiment shown in FIG. 21, a relatively narrow insertion hole 70 is formed through a peripheral wall of a body 1. A pair of projections 13 and 14 are formed on the inner peripheral surface of the body 1, and spaced from each other along the length of the body 1. The two projections 13 and 14 are disposed in opposed relation to each other, with the insertion hole 70 disposed therebetween. The construction and operation of the projections 13 and 14 are the same as those described above for the embodiment of FIGS. 1 to 4. An operating member 71 is integrally formed on the outer peripheral surface of the body 1 through a neck portion 72 disposed forwardly of the insertion hole 70. The operating member 71 extends rearwardly from the neck portion 72 along the length of the body 1. A projection 73 is formed on the distal end of the operating member 71 remote from the neck portion 72, and is passed through the insertion hole 70. When the operating member 71 is pressed toward the body 1, the projection 73 presses a wire 11, so that the wire 11 is pulled to bend a bending portion.

Figure 22:
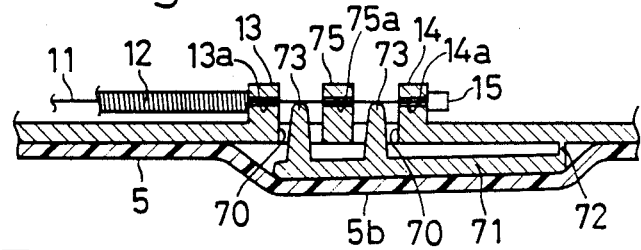

In an embodiment shown in FIG. 22, another projection 75 is formed on an inner peripheral surface of a body 1, and disposed between two projections 13 and 14. An insertion hole 70 is formed through that portion of the peripheral wall of the body 1 lying between the projections 13 and 75, and another insertion hole 70 is formed through that portion of the peripheral wall of the body 1 lying between the projections 75 and 14. The projection 75 has an insertion hole 75a through which a wire 11 is passed. An operating member 71 is formed integrally on the outer peripheral surface of the body 1 through a neck portion 72 disposed rearwardly of the rear insertion hole 70. The operating member 71 extends forwardly from the neck portion 72 along the length of the body 1. Two projections 73 are formed on the distal end portion of the operating member 71 remote from the neck portion 72, and are passed through the two insertion holes 70, respectively. When the operating member 71 is pressed, the two projections 73 simultaneously press that portion of the wire 11 disposed between the projections 13 and 75 and that portion of the wire 11 disposed between the projections 75 and 14. As a result, the wire 11 is pulled an amount twice larger than that achieved in embodiment of FIG. 21, so that the amount of bending of a bending portion can be increased.

Figure 23:
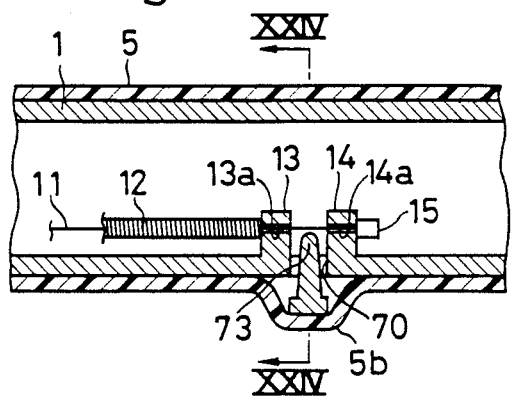
Figure 24:
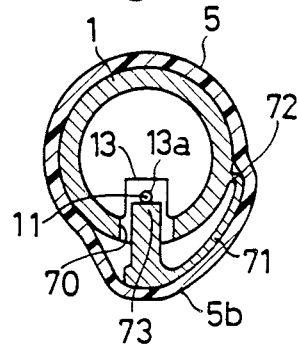
FIG. 24 is a cross-sectional view taken along the line XXIV—XXIV of FIG. 23.

In an embodiment shown in FIGS. 23 and 24, an operating member 71 extends in a circumferential direction of a body 1 outside of the body 1.

Figure 25:
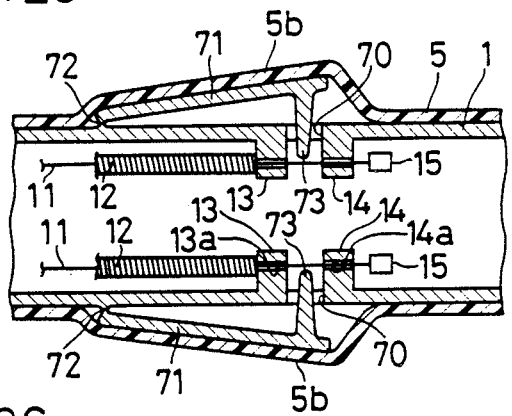
FIGS. 25 to 27 are cross-sectional views of important portions of further modified bending devices, respectively.

In an embodiment shown in FIG. 25, a bending portion is adapted to be bend in two directions, for example, in upward and downward directions. This embodiment is similar in basic construction to the embodiment of FIG. 21. More specifically, two pairs of projections 13 and 14 are formed on a body 1 to support a pair of wires 11, respectively, and two insertion holes 70 are formed through the peripheral wall of the body 1. Two operating members 71 are integrally formed with the body 1. For the same reasons described above for the embodiment of FIG. 6, a pair of stop members 15 fixedly connected respectively to the proximal ends of the two wires 11 are spaced apart from the two projections 14, respectively.

Figure 26:
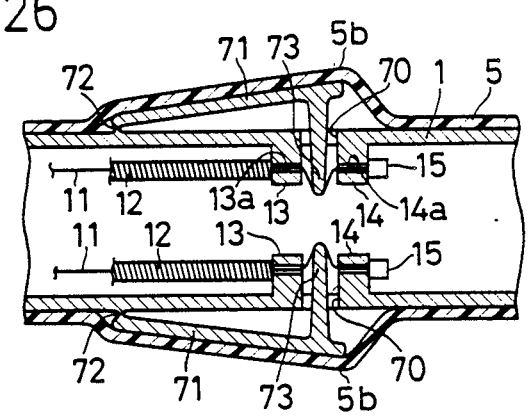

An embodiment shown in FIG. 26 is identical to the embodiment of FIG. 25 except for the following points. When a bending portion is in a straight condition, that portion of each wire 11 disposed between projections 13 and 14 is pushed and bent by a projection 73 of a respective one of operating members 71. Each stop member 15 is abutted against the corresponding projection 14. In this embodiment, when one of the operating members 71 is pressed, the bending portion immediately begins to be bent since the stop member 15 is abutted against the projection 14 from the beginning. As the bending portion is bent, the other wire 11 is pulled, so that the other operating member 71 is pushed by the other wire 11 to be pivotally moved in a direction away from the body 1.

Figure 27:
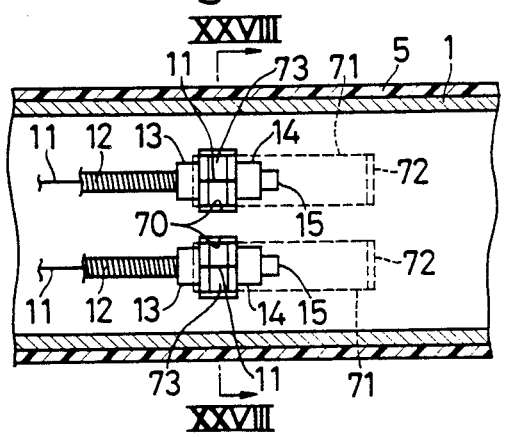
Figure 28:
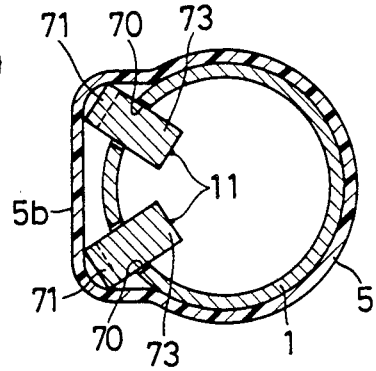
FIG. 28 is a cross-sectional view taken along the line XXVIII—XXVIII of FIG. 27.

An embodiment shown in FIGS. 27 and 28 is basically similar to the embodiment of FIG. 26, but differs therefrom only in that two operating members 71 are arranged close to each other in a direction of a circumference of a body 1.

Figure 29:
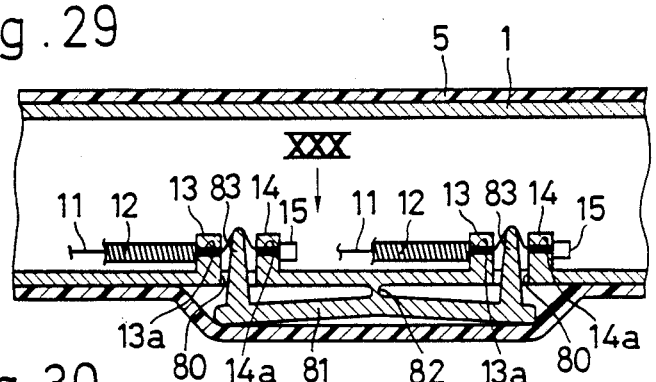
FIG. 29 is a cross-sectional view of an important portion of a further modified bending device.
Figure 30:
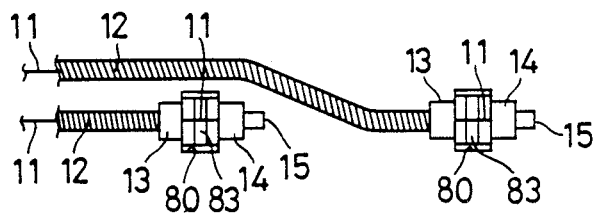
FIG. 30 is a view as seen in a direction indicated by arrow XXX of FIG. 29.

In an embodiment shown in FIGS. 29 and 30, a pair of insertion holes 80 are formed through a peripheral wall of a body 1, and are spaced from each other along the length of the body 1. Two pairs of projections 13 and 14 are formed on the inner peripheral surface of the body 1, and are spaced from each other along the length of the body 1, and are aligned with each other in the longitudinal direction of the body 1. A guide tube 12 fixedly connected at its proximal end to the right projection 13 close to the proximal end of the body 1, as well as a wire 11 fixedly connected at its proximal end to the right projection 14, extends toward an insertion portion in a manner to avoid the other pair of projections 13 and 14. An operating member 81 is integrally formed at its central portion on the outer peripheral surface of the body 1 through a neck portion 82. The neck portion 82 is disposed midway between the two insertion holes 80. The operating member 81 extends from the neck portion 82 forwardly and rearwardly along the length of the body 1, and a pair of projections 83 are formed on the opposite ends of the operating member 81, respectively. The two projections 83 are passed respectively through the two insertion holes 80, and are held against the two wires 11, respectively.

In this embodiment, when the front end of the operating member 81 is pressed, one wire 11 is pulled to bend the bending portion upwardly. When the rear end of the operating member 81 is pressed, the other wire 11 is pulled to bend the bending portion downwardly.

Figure 31:
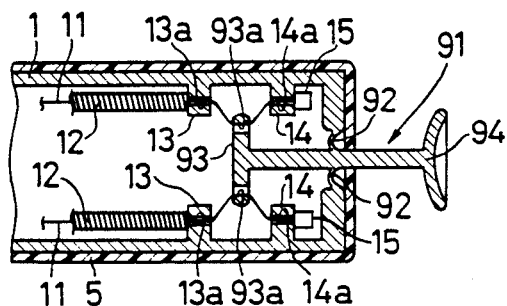
FIGS. 31 and 32 are cross-sectional views of important portions of further modified bending devices, respectively.

FIG. 31 shows an embodiment of the invention directed to a medical catheter. The catheter is designed to be inserted into a blood vessel, and is not provided with inspection means. In this embodiment, a joy stick (operating member) 91 is formed integrally with a body 1 at a proximal end thereof. More specifically, the joy stick 91 is integrally connected through a pair of neck portions 92 to the body 1 at its upper and lower surfaces intermediate its opposite ends of the joy stick 91, and is pivotally movable in upward and downward directions (FIG. 31). An engaging portion 93 is formed on the inner end of the joy stick 91, and extends perpendicular to the axis of the joy stick 91. Holes 93a are formed through the opposite ends of the engaging portion 93, respectively, and two wires 11 are passed respectively through the holes 93a and are engaged with the engaging portion 93. The joy stick 91 has it its outer end a receptive portion 94 for receiving the thumb. In this embodiment, the receptive portion 94 of the joy stick 91 is moved upward to pivotally move the joy stick 91, so that the engaging portion 93 is moved downward to pull the upper wire 11, thereby bending a bending portion upwardly. In contrast, when the receptive portion 94 of the joy stick 91 is moved downward, the bending portion is bent downwardly.

Figure 32:
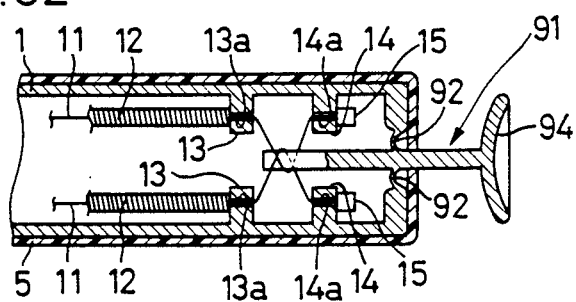

In an embodiment shown in FIG. 32, an inner end portion of a joy stick 91 serves as an engaging portion, and two wires 11 are extended or turned around this engaging portion over a half of the circumference thereof, and are engaged with the engaging portion.

The present invention is not to be restricted to the above embodiments, and modifications can be made without departing from the spirits of the invention.

In each of the above embodiments, although each projection has the insertion hole for passing the wire therethrough, the insertion hole may be replaced by a slit The constructions shown in FIGS. 1 to 30 can be applied not only to the endoscope but also to a catheter The constructions shown in FIGS. 31 and 32 may be applied to an endoscope.

The construction of each of the above embodiments can be applied to an endoscope or a catheter of the type in which the bending portion can be bent in a desired number of directions.

What is claimed is:
1. A bending device comprising:
  (a) a hollow body;
  (b) an insertion portion extending from said body;
  (c) a bending portion extending from a distal end of said insertion portion; and
  (d) a wire fixedly connected at its distal end to a distal end of said bending portion and having a proximal end disposed in said body, said wire extending through said bending portion and said insertion portion into said body;
  (e) said body having a manipulation hole into which the finger is adapted to be inserted, a guide portion through which said wire is passed and a retainer portion for retaining the proximal end of said wire being formed on an inner surface of said body, said guide portion and said retainer portion being disposed in opposed relation to each other, said manipulation hole being disposed between said guide portion and said retainer portion, part of said wire being disposed in said manipulation hole, and said wire receiving a force applied, in a direction perpendicular to a longitudinal direction of said wire, by the finger inserted in said manipulation hole, so that said wire is pulled to bend said bending portion.

2. A bending device according to claim 1, in which said body has a tubular shape, said insertion portion extending from a distal end of said body, part of a peripheral wall of said body being removed intermediate the opposite ends of said body to provide said manipulation hole, and said guide portion and said retainer portion being spaced from each other along the length of said body.

3. A bending device according to claim 2, further comprising an elastic sheath tube intimately fitted entirely around at least that portion of said body having said manipulation hole, so that said sheath tube closes said manipulation hole.

4. A bending device according to claim 2, in which in a direction of insertion of the finger, part of a peripheral edge of said manipulation hole is disposed closer to an axis of said body than said part of said wire.

5. A bending device comprising:
  (a) a hollow body having a manipulation hole into which the finger is adapted to be inserted;
  (b) an insertion portion extending from said body;
  (c) a bending portion extending from a distal end of said insertion portion;
  (d) a wire fixedly connected at its distal end to a distal end of said bending portion and having a proximal end disposed in said body, said wire extending through said bending portion and said insertion portion and into said body; and
  (e) operating means for converting a force, applied by the finger inserted into said manipulation hole, into a force to pull said wire so as to bend said bending portion, said operating means being disposed inside of said body in opposed relation to said manipulation hole.

6. A bending device according to claim 5, in which said body has a tubular shape, said insertion portion extending from a distal end of said body, said manipulation hole being formed through a peripheral wall of said body intermediate the opposite ends of said body, first and second support members being formed on an inner surface of said body in opposed relation to each other and spaced from each other along the length of said body, said manipulation hole being disposed between said first and second support members, said first support member being disposed remote from a proximal end of said body whereas said second support member is disposed close to said proximal end of said body, said operating means comprising a first link, a second link and a third link, said first link being supported on said first support member for sliding movement along the length of said body, said second link being pivotally connected at its proximal end to said second support member, said third link being pivotally connected at its distal end to a proximal end of said first link and pivotally connected at its proximal end to a distal end of said second link, an axis of pivotal movement of said second link relative to said second support member and axes of pivotal movement of said third link relative to said first and second links being disposed perpendicular to the axis of said body and also perpendicular to a direction of insertion of the finger, a portion of pivotal connection between the distal end of said second link and the proximal end of said third link being disposed in said manipulation hole, and upon pressing of said connection portion by the finger, said wire being pulled to bend said bending portion.

7. A bending portion according to claim 5, in which said body has a tubular shape, said insertion portion extending from a distal end of said body, said manipulation hole being formed through a peripheral wall of said body intermediate the opposite ends of said body, a pair of support members being formed on an inner surface of said body in opposed relation to each other and spaced from each other along the length of said body, said manipulation hole being disposed between said pair of support members, there being provided a guide tube serving as said operating means, said wire being passed through said guide tube, said guide tube being fixedly connected at its distal end to the proximal end of said bending portion, and extending through said insertion portion into said body, said guide tube being slidably passed through said pair of support members, said guide tube being fixedly connected at its proximal end to the proximal end of said wire, and when that portion of said guide tube disposed between said pair of support members is pressed by the finger inserted in said manipulation hole, so that said that portion is bent in a direction substantially perpendicular to a longitudinal direction of said guide tube, said wire being pulled to bend said bending portion.

8. A bending device comprising:
(a) a hollow body;
(b) an insertion portion extending from said body;
(c) a bending portion extending from a distal end of said insertion portion;
(d) a wire fixedly connected at its distal end to a distal end of said bending portion and having a proximal end disposed in said body, said wire extending through said bending portion and said insertion portion and into said body; and
(e) an operating member slidably supported on said body, said operating member being operatively connected to said wire, and upon sliding movement of said operating member relative to said body, said wire being pulled to bend said bending portion.

9. A bending device according to claim 8, in which said body has a tubular shape, said insertion portion extending from a distal end of said body, a pair of opposed guide holes being formed through a peripheral wall of said body intermediate the opposite ends of said body, and spaced 180° from each other in a direction of the periphery of said body, said operating member being elongated and extending through said pair of guide holes for sliding movement in a direction perpendicular to the longitudinal direction of said body, a guide portion through which said wire is passed and a retainer portion for retaining the proximal end of said wire being formed on an inner surface of said body, said operating member having engaging means engaged with that portion of said wire disposed between said guide portion and said retainer portion, and upon sliding movement of said operating member, said wire being pulled by said engaging means to bend said bending portion.

10. A bending device according to claim 9, in which said guide portion and said retainer portion are spaced from each other along the length of said body and are disposed in opposed relation to each other, said guide hole being disposed between said guide portion and said retainer portion, and upon sliding movement of said operating member, said engaging means applying a force to that portion of said wire disposed between said guide portion and said retainer portion in a direction substantially perpendicular to the longitudinal direction of said wire, so that said wire is pulled.

11. A bending device according to claim 10, further comprising a second wire fixedly connected at its distal end to a distal end of said bending portion and having a proximal end disposed in said body, said second wire extending through said bending portion and said insertion portion into said body, those portions of the distal end of said bending portion to which said first-mentioned wire and said second wire are fixedly connected, respectively, being spaced 180° from each other in a direction of a periphery of said bending portion, a second guide portion through which said second wire is passed and a second retainer portion for retaining the proximal end of said second wire being formed on an inner surface of said body, said first-mentioned guide portion and retainer portion being spaced 180° from said second guide portion and retainer portion in a direction of a periphery of said body, that portion of said second wire disposed between said second guide portion and said second retainer portion being also engaged with said engaging means of said operating member, the opposite ends of said operating member being projected outwardly from said body when said operating member is in its inoperative condition, when one of the opposite ends of said operating member is pressed, one of said two wires being pulled to bend said bending portion in one direction, and when the other end of said operating member is pressed, the other wire being pulled to bend said bending portion in a direction opposite to said one direction.

12. A bending device according to claim 9, further comprising an elastic sheath tube intimately fitted entirely around at least that portion of said body where said guide holes and the opposite ends of said operating member are disposed, so that said sheath tube covers said guide holes and the opposite ends of said operating member.

13. A bending device comprising:
(a) a hollow body of a resin;
(b) an insertion portion extending from said body;
(c) a bending portion extending from a distal end of said insertion portion;
(d) a wire fixedly connected at its distal end to a distal end of said bending portion and having a proximal end disposed in said body, said wire extending through said bending portion and said insertion portion into said body; and
(e) an operating member integrally formed on said body through a neck portion integral with said body, said operating member being pivotal about said neck portion, said operating member being operatively connected to said wire, and upon pivotal movement of said operating member, said wire being pulled to bend said bending portion.

14. A bending device according to claim 13, in which said body has a tubular shape, said insertion portion extending from a distal end of said body, said operating member being connected to a peripheral wall of said body through said neck portion intermediate opposite ends of said body, and at least part of said operating member being projected outwardly from the peripheral wall of said body.

15. A bending device according to claim 14, further comprising a elastic sheath tube intimately fitted entirely around at least that portion of said body where said operating member is provided, so that said sheath tube covers said operating member.

16. A bending device according to claim 14, in which part of the peripheral wall of said body is reduced in thickness to provide said neck portion, said wire being connected to that portion of said operating member received in said body.

17. A bending device according to claim 14, in which an insertion hole is formed through the peripheral wall of said body, a guide portion through which said wire is passed and a retainer portion for retaining the proximal end of said wire being formed on an inner surface of said body, said guide portion and said retainer portion being disposed in opposed relation to each other and spaced from each other along the length of said body, said insertion hole being disposed between said guide portion and said retainer portion, part of said wire being opposed to said insertion hole, said operating member being connected at its proximal end to an outer peripheral surface of said body through said neck portion spaced from said insertion hole, said operating member extending from said neck portion to said insertion hole, said operating member having at its distal end a projection inserted in said insertion hole, and upon pressing of said operating member toward said body, said projection of said operating member urging said wire in a direction perpendicular to the longitudinal direction of said wire to pull said wire, thereby bending said bending portion.

18. A bending device according to claim 13, in which said operating member comprises a joy stick provided on that side of said body opposite to said insertion portion, said joy stick being integrally connected to said body through said neck portion intermediate the opposite ends of said joy stick, said joy stick having, at its outer end disposed exteriorly of said body, a receptive portion for receiving a manipulating force of the finger, and said wire being engaged with an inner end of said joy stick disposed in said body.

19. A bending device according to claim 18, in which a guide portion through which said wire is passed and a retainer portion for retaining the proximal end of said wire being formed on an inner surface of said body, that portion of said wire disposed between said guide portion and said retainer portion being engaged with the inner end of said joy stick.

* * * * *